(12) United States Patent
Michihata et al.

(10) Patent No.: US 11,033,174 B2
(45) Date of Patent: Jun. 15, 2021

(54) MEDICAL IMAGE PROCESSING DEVICE AND MEDICAL OBSERVATION DEVICE

(71) Applicant: Sony Olympus Medical Solutions Inc., Tokyo (JP)

(72) Inventors: Taihei Michihata, Kanagawa (JP); Yuichi Yamada, Tokyo (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 41 days.

(21) Appl. No.: 16/455,773

(22) Filed: Jun. 28, 2019

(65) Prior Publication Data

US 2020/0008650 A1    Jan. 9, 2020

(30) Foreign Application Priority Data

Jul. 6, 2018  (JP) .............................. JP2018-128862

(51) Int. Cl.
| | |
|---|---|
| G06K 9/00 | (2006.01) |
| A61B 1/00 | (2006.01) |
| A61B 1/04 | (2006.01) |
| A61B 1/06 | (2006.01) |
| A61B 1/05 | (2006.01) |
| A61B 90/00 | (2016.01) |
| A61B 90/20 | (2016.01) |

(52) U.S. Cl.
CPC ...... *A61B 1/00009* (2013.01); *A61B 1/00006* (2013.01); *A61B 1/042* (2013.01); *A61B 1/0661* (2013.01); *A61B 1/00045* (2013.01); *A61B 1/00188* (2013.01); *A61B 1/053* (2013.01); *A61B 1/0638* (2013.01); *A61B 1/0646* (2013.01); *A61B 90/20* (2016.02); *A61B 90/361* (2016.02)

(58) Field of Classification Search
CPC ...... G06K 9/6423; G06K 9/32; G06K 9/6407; G06K 9/686; G06K 9/2009; A61B 1/00009; A61B 1/042; A61B 1/00006; A61B 1/0661; A61B 1/053; G06T 7/001; G06F 17/30249

See application file for complete search history.

(56) References Cited

U.S. PATENT DOCUMENTS

| | | | | |
|---|---|---|---|---|
| 5,131,382 A | * | 7/1992 | Meyer | .................... A61B 1/042 600/104 |
| 5,928,137 A | * | 7/1999 | Green | ................ A61B 1/00052 600/104 |

(Continued)

FOREIGN PATENT DOCUMENTS

JP    2015-156937 A    9/2015

*Primary Examiner* — Amir Alavi
(74) *Attorney, Agent, or Firm* — Xsensus, LLP

(57) ABSTRACT

A medical image processing device includes a motion amount calculating unit configured to compare a first image obtained by capturing a subject image taken by an endoscope with a second image obtained by capturing the subject image at a chronologically different timing from the first image and calculate a motion amount for the second image every two or more areas in the first image; and an area specifying unit configured to specify a mask area other than the subject image included in the first image from an inside of a mask candidate area in which the motion amount is equal to or less than a specific first threshold value in the first image.

12 Claims, 8 Drawing Sheets

(56) References Cited

U.S. PATENT DOCUMENTS

| | | | | |
|---|---|---|---|---|
| 7,303,528 | B2* | 12/2007 | Couvillon, Jr. | A61B 1/00059 600/118 |
| 8,672,836 | B2* | 3/2014 | Higgins | A61B 90/36 600/117 |
| 8,942,530 | B2* | 1/2015 | Demers | A61B 1/00144 385/117 |
| 9,186,041 | B2* | 11/2015 | Kasumi | A61B 1/0005 |
| 2005/0014996 | A1* | 1/2005 | Konomura | G02B 23/2476 600/175 |
| 2005/0073578 | A1* | 4/2005 | Odlivak | G16H 10/60 348/65 |
| 2013/0038689 | A1* | 2/2013 | McDowall | A61B 1/00045 348/45 |
| 2014/0323806 | A1* | 10/2014 | Brain | A61B 1/00154 600/115 |
| 2018/0092515 | A1* | 4/2018 | Yashiro | A61B 1/00181 |
| 2020/0008650 | A1* | 1/2020 | Michihata | A61B 1/00009 |

* cited by examiner

MEDICAL IMAGE PROCESSING DEVICE AND MEDICAL OBSERVATION DEVICE

CROSS-REFERENCE TO RELATED APPLICATION

The present application claims priority to and incorporates by reference the entire contents of Japanese Patent Application No. 2018-128862 filed in Japan on Jul. 6, 2018.

BACKGROUND

The present disclosure relates to a medical image processing device and a medical observation device.

In the past, a medical image processing device that processes a captured image obtained by imaging an inside of a subject of human or the like (an inside of a living organism) has been known (see, for example, JP 2015-156937 A).

The medical image processing device described in JP 2015-156937 A acquires a captured image. The captured image includes a subject image taken by an endoscope inserted into a living organism. Here, light (subject image) taken by the endoscope has a substantially circular cross section. Therefore, the subject image in the captured image is substantially circular. In other words, the captured image includes the subject image and a mask area other than the subject image. Then, the medical image processing device converts the acquired captured image into a luminance image and specifies the mask area using a luminance distribution in the luminance image.

SUMMARY

In a case in which a subject when the mask area is specified is, for example, a white subject such as a gauze, a luminance value of the subject image included in the captured image is sufficiently high. Therefore, the mask area may be specified with high accuracy using the luminance distribution in the captured image. However, when imaging, it is necessary to cover a distal end of the endoscope with a white subject such as gauze during imaging, and thus there is a problem in that a task is complicated.

On the other hand, in a case in which the subject when the mask area is specified is not the above-described subject, a variation in the luminance value of the subject image included in the captured image becomes large. Therefore, there is a problem in that it is difficult to specify the mask area with high accuracy using the luminance distribution in the captured image.

In this regard, there is a need for a technology capable of specify the mask area easily and accurately.

A medical image processing device according to one aspect of the present disclosure includes: a motion amount calculating unit configured to compare a first image obtained by capturing a subject image taken by an endoscope with a second image obtained by capturing the subject image at a chronologically different timing from the first image and calculate a motion amount for the second image every two or more areas in the first image; and an area specifying unit configured to specify a mask area other than the subject image included in the first image from an inside of a mask candidate area in which the motion amount is equal to or less than a specific first threshold value in the first image.

DETAILED DESCRIPTION

Figure 1:
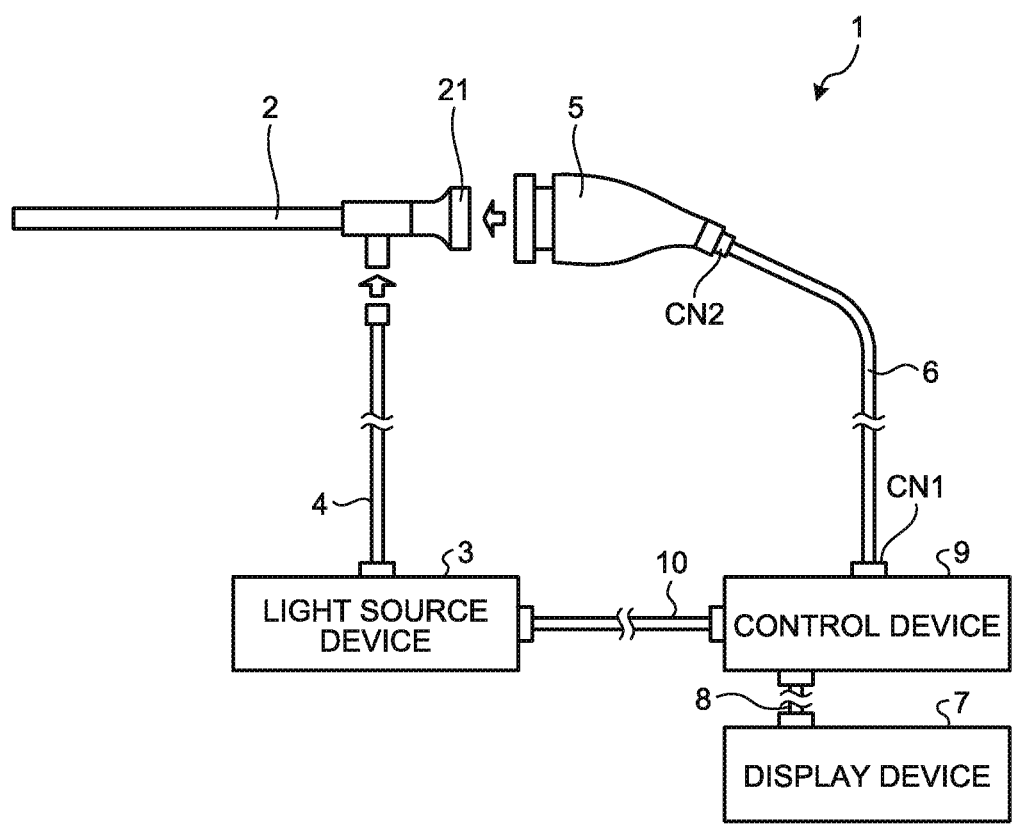
FIG. 1 is a diagram illustrating a configuration of a medical observation device in accordance with an embodiment.

Hereinafter, a mode (hereinafter an "embodiment") for carrying out the present disclosure will be described with reference to the appended drawings. The present disclosure is not limited by an embodiment to be described below. Further, in the drawings, the same parts are given the same reference numerals.

Schematic Configuration of Medical Observation Device

FIG. 1 is a diagram illustrating a configuration of a medical observation device 1 according to the present embodiment.

A medical observation device 1 is a device which is used in a medical field and observes an inside of a living organism. This medical observation device 1 includes an inserting unit 2, a light source device 3, a light guide 4, a camera head 5, a first transmission cable 6, a display device 7 and a second transmission cable 8, a control device 9, and a third transmission cable 10 as illustrated in FIG. 1.

The inserting unit 2 corresponds to an endoscope according to the present disclosure. In the present embodiment, the inserting unit 2 includes a rigid endoscope. In other words, the inserting unit 2 has an elongated shape which is entirely rigid or partially flexible and partially rigid and is inserted into a living organism. An optical system which is constructed using one or more lenses and condenses a subject image is installed in the inserting unit 2.

The light source device 3 is connected to one end of the light guide 4 and supplies light for illuminating the inside of the living organism to one end of the light guide 4 under the control of the control device 9. In the present embodiment, the light source device 3 is configured separately from the control device 9, but the present disclosure is not limited to this example, and a configuration installed in the control device 9 may be employed.

One end of the light guide 4 is detachably connected to the light source device 3, and the other end thereof is detachably connected to the inserting unit 2. The light guide 4 transfers the light supplied from the light source device 3 from one end to the other end and supplies the light to the inserting unit 2. The light supplied to the inserting unit 2 is emitted from the distal end of the inserting unit 2 and irradiated into the living organism. The light (subject image) which is emitted into the living organism and reflected in the living organism is collected by the optical system in the inserting unit 2.

The camera head 5 corresponds to an imaging device according to the present disclosure. The camera head 5 is detachably connected to a proximal end (an eyepiece 21 (FIG. 1)) of the inserting unit 2. The camera head 5 captures the subject image collected by the inserting unit 2 under the control of the control device 9 and outputs an image signal (a RAW signal) by the imaging. The image signal is, for example, an image signal of 4K or more.

A detailed configuration of the camera head 5 will be described later.

One end of the first transmission cable 6 is detachably connected to the control device 9 via a connector CN1 (FIG. 1), and the other end is detachably connected to the camera head 5 via a connector CN2 (FIG. 1). The first transmission cable 6 transmits the image signal or the like output from the camera head 5 to the control device 9, and a control signal, a synchronization signal, a clock, electric power, and the like output from the control device 9 are transmitted to the camera head 5.

Further, the transmission of the image signal or the like from the camera head 5 to the control device 9 via the first transmission cable 6 may be performed by an optical signal or the like or may performed by an electrical signal. The same applies to the transmission of the control signal, the synchronization signal, and the clock from the control device 9 to the camera head 5 via the first transmission cable 6.

The display device 7 is constituted by a display using a liquid crystal or organic electroluminescence (EL), or the like, and displays an image based on a video signal from the control device 9 under the control of the control device 9.

One end of the second transmission cable 8 is detachably connected to the display device 7, and the other end is detachably connected to the control device 9. The second transmission cable 8 transmits the video signal processed by the control device 9 to the display device 7.

The control device 9 corresponds to a medical image processing device according to the present disclosure. The control device 9 includes a central processing unit (CPU) or the like, and controls the operations of the light source device 3, the camera head 5, and the display device 7 in general.

A detailed configuration of the control device 9 will be described later.

One end of the third transmission cable 10 is detachably connected to the light source device 3, and the other end is detachably connected to the control device 9. The third transmission cable 10 transmits the control signal from the control device 9 to the light source device 3.

Configuration of Camera Head

Next, a configuration of the camera head 5 will be described.

Figure 2:
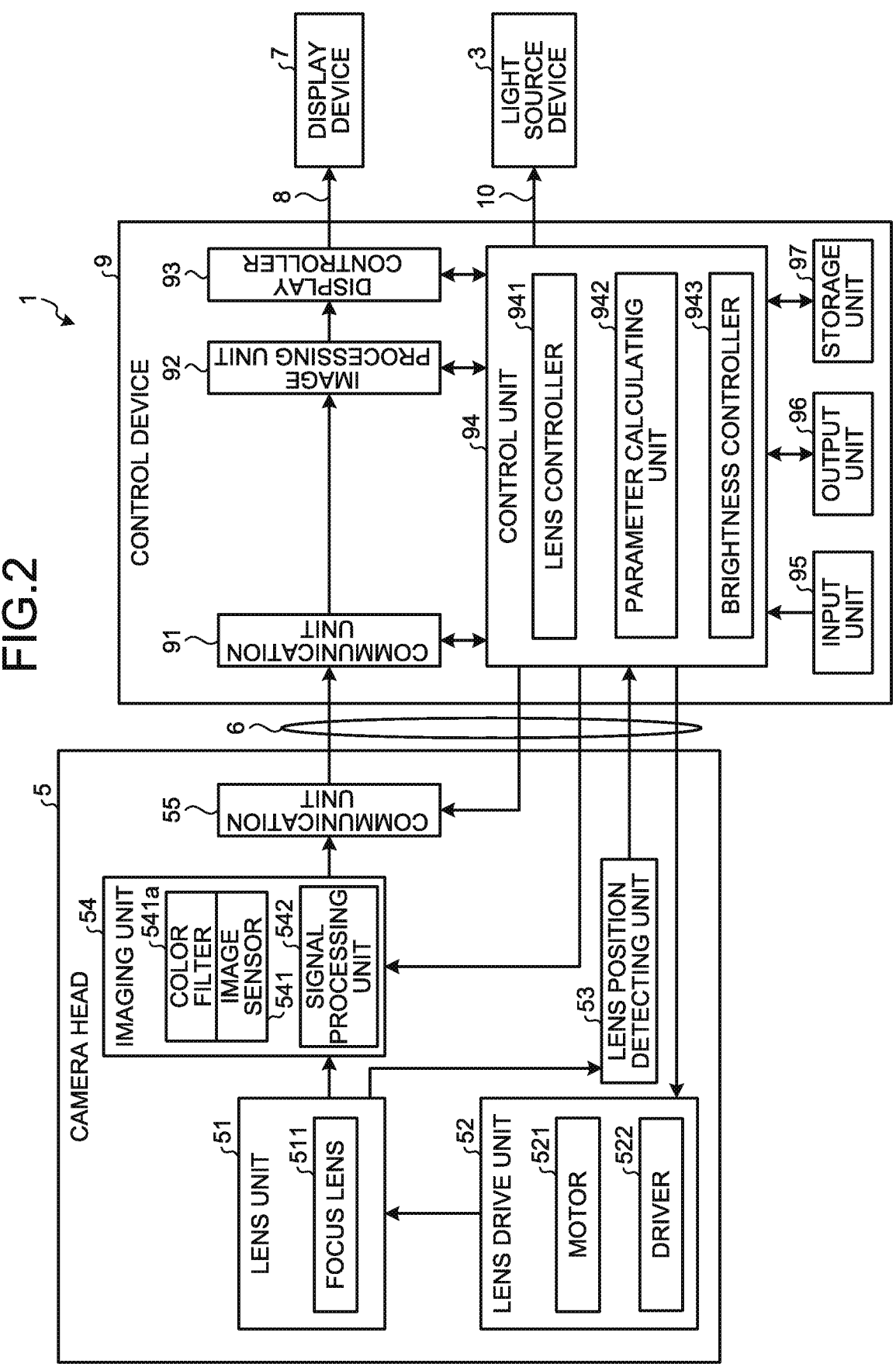
FIG. 2 is a block diagram illustrating a configuration of a camera head and control device.

FIG. 2 is a block diagram illustrating configurations of the camera head 5 and the control device 9.

In FIG. 2, for convenience of description, illustration of the connectors CN1 and CN2 between the control device 9 and the camera head 5 and the first transmission cable 6, the connector between the control device 9 and the display device 7 and the second transmission cable 8, and the connector between the control device 9 and the light source device 3 and the third transmission cable 10 is omitted.

The camera head 5 includes a lens unit 51, a lens drive unit 52, a lens position detecting unit 53, an imaging unit 54, and a communication unit 55 as illustrated in FIG. 2.

The lens unit 51 is configured using a plurality of lenses movable along an optical axis, and the subject image collected by the inserting unit 2 is formed on an imaging surface of the imaging unit 54 (an image sensor 541 (FIG. 2)). The lens unit 51 includes a focus lens 511 as illustrated in FIG. 2.

The focus lens 511 is configured using one or more lenses and adjusts a focus by moving along the optical axis.

Also, a focusing mechanism (not illustrated) for moving the focus lens 511 along the optical axis is installed in the lens unit 51.

The lens drive unit 52 includes a motor 521 that operates the above-described focusing mechanism and a driver 522 that drives the motor 521 as illustrated in FIG. 2. The lens drive unit 52 adjusts the focus of the lens unit 51 under the control of the control device 9.

The lens position detecting unit 53 is configured using a position sensor such as a photo interrupter and detects a lens position of the focus lens 511 (hereinafter referred to as a "focus position"). The lens position detecting unit 53 outputs a detection signal corresponding to the focus position to the control device 9 via the first transmission cable 6.

The imaging unit 54 images the inside of the living organism under the control of the control device 9. The imaging unit 54 includes an image sensor 541 and a signal processing unit 542 as illustrated in FIG. 2.

The image sensor 541 is constituted by a charge coupled device (CCD), a complementary metal oxide semiconductor (CMOS), or the like that receives the subject image which is collected by the inserting unit 2 and formed by the lens unit 51 and converts it into an electrical signal (analog signal).

Here, a color filter 541*a* (FIG. 2) in which three filter groups grouped in accordance with wavelength bands of light to be transmitted (R (red), G (green), and B (blue)) are arranged in a predetermined format (for example, a Bayer array) is installed on the imaging surface (a light receiving surface) of the image sensor 541.

Specifically, the color filter 541*a* includes an R filter group which transmits light of a wavelength band of R, a B filter group which transmits light of a wavelength band of B, a first G filter group which transmits light of a wavelength band of G (arranged in the same column as the R filter group), and a second G filter group which transmits light of a wavelength band of G (arranged in the same column as the B filter group). Hereinafter, for convenience of description, the first and second G filter groups are referred to collectively as a "G filter group".

In other words, the electric signal (analog signal) from the image sensor 541 includes, for each pixel, component information (pixel value) of any one of R, G, and B corresponding to each of the R, G, and B filter groups.

The signal processing unit 542 performs signal processing on the electrical signal (analog signal) from the image sensor 541 and outputs an image signal (a RAW signal (a digital signal)).

For example, the signal processing unit 542 performs a process of removing reset noise, a process of amplifying an analog signal, a process of multiplying an analog gain, and signal processing such as an A/D conversion on the electric signal (analog signal) from the image sensor 541.

The communication unit 55 functions as a transmitter that transmits the image signal (the RAW signal (the digital signal)) output from the imaging unit 54 to the control device 9 via the first transmission cable 6. The communication unit 55 is constituted by, for example, a high-speed serial interface that performs communication of the image signal with the control device 9 at a transmission rate of 1 Gbps or more via the first transmission cable 6.

Configuration of Control Device

Next, a configuration of the control device 9 will be described with reference to FIG. 2.

The control device 9 includes a communication unit 91, an image processing unit 92, a display controller 93, a control unit 94, an input unit 95, an output unit 96, and a storage unit 97 as illustrated in FIG. 2.

The communication unit 91 functions as a receiver that receives the image signal (the RAW signal (the digital signal)) output from the camera head 5 (the communication unit 55) via the first, transmission cable 6. The communication unit 91 is constituted by, for example, a high-speed serial interface that performs communication of the image signal with the communication unit 55 at a transmission rate of 1 Gbps or more.

Figure 3:
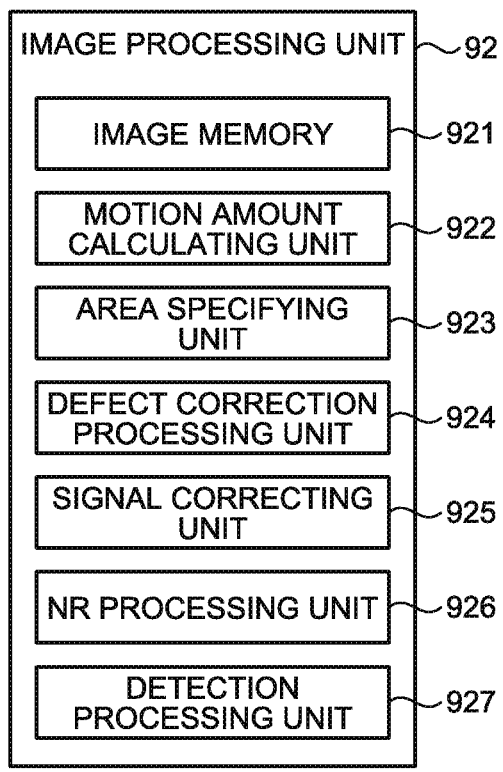
FIG. 3 is a block diagram illustrating a configuration of an image processing unit.

FIG. 3 is a block diagram illustrating a configuration of the image processing unit 92.

The image processing unit 92 processes the image signal (the RAW signal (the digital signal)) which is output from the camera head 5 (communication unit 55) and received by the communication unit 91 under the control of the control unit 94. The image processing unit 92 includes an image memory 921, a motion amount calculating unit 922, an area specifying unit 923, a defect correction processing unit 924, a signal correcting unit 925, an NR processing unit 926, and a detection processing unit 927 as illustrated in FIG. 3.

The image memory 921 sequentially stores the image signal (the RAW signal (the digital signal)) which is output from the camera head 5 and received by the communication unit 91 in units of frames by a predetermined number of frames. In other words, the image signals corresponding to a predetermined number of frames (the captured images corresponding to a predetermined number of frames) stored in the image memory 921 are sequentially rewritten as captured images newly captured by the camera head 5.

The motion amount calculating unit 922 executes a motion amount calculation process of comparing the captured image (hereinafter referred to as a "current captured image") which is output from the camera head 5 and received by the communication unit 91 with a captured image (hereinafter referred to as a "previous captured image") which is captured by the camera head 5 chronologically immediately before (one frame earlier than) the current captured image and stored in the image memory 921 and calculating a motion amount for the previous captured image for each area (for each pixel in the present embodiment) in the current captured image. The current captured image corresponds to a first image according to the present disclosure. Also, the previous captured image corresponds to a second image according to the present disclosure. Here, the second image according to the present disclosure is not limited to the previous captured image, but as long as it is a captured image captured by the camera head 5 at a timing chronologically different from the current captured image, a captured image captured prior to several frames may be used, or a captured image captured after one frame or several frames may be used. Further, the current captured image and the previous captured image used in the motion amount calculation process may be images before a demosaic process performed by the signal correcting unit 925 or may be images which have undergone the demosaic process. Further, the motion amount calculation process is not limited to the process of calculating a motion amount for all areas (all pixels) in the current captured image, but a process of calculating a motion amount only for some areas among all areas (some pixels among all pixels) in the current captured image may be used.

Figure 4:
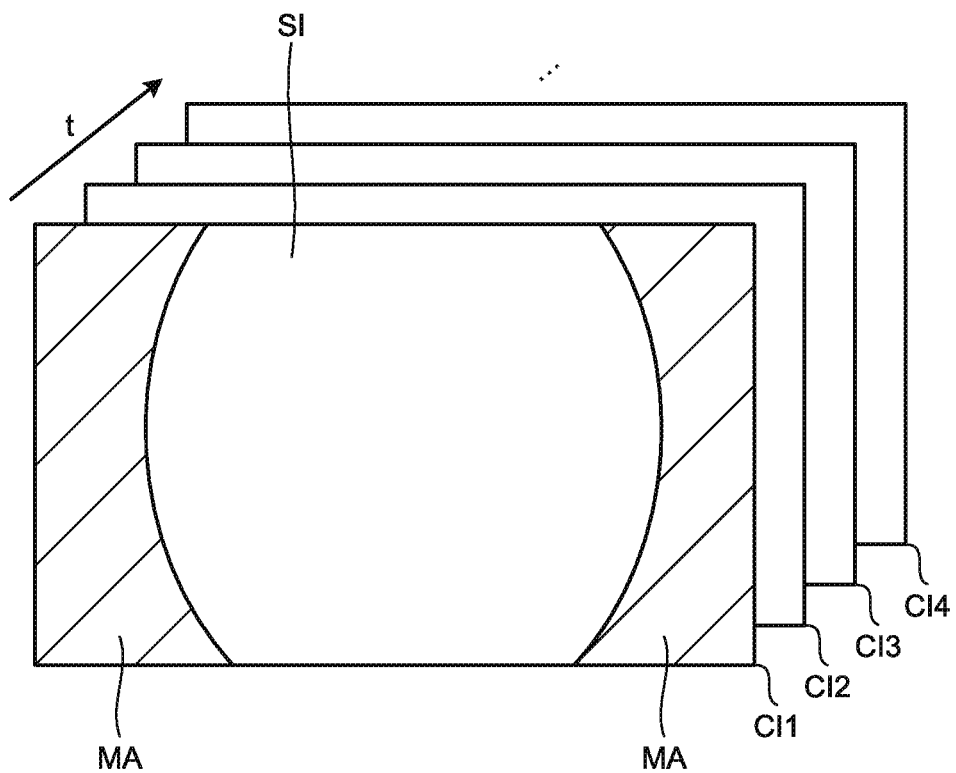
FIG. 4 is a diagram illustrating an example of a motion amount calculation process.
Figure 5:
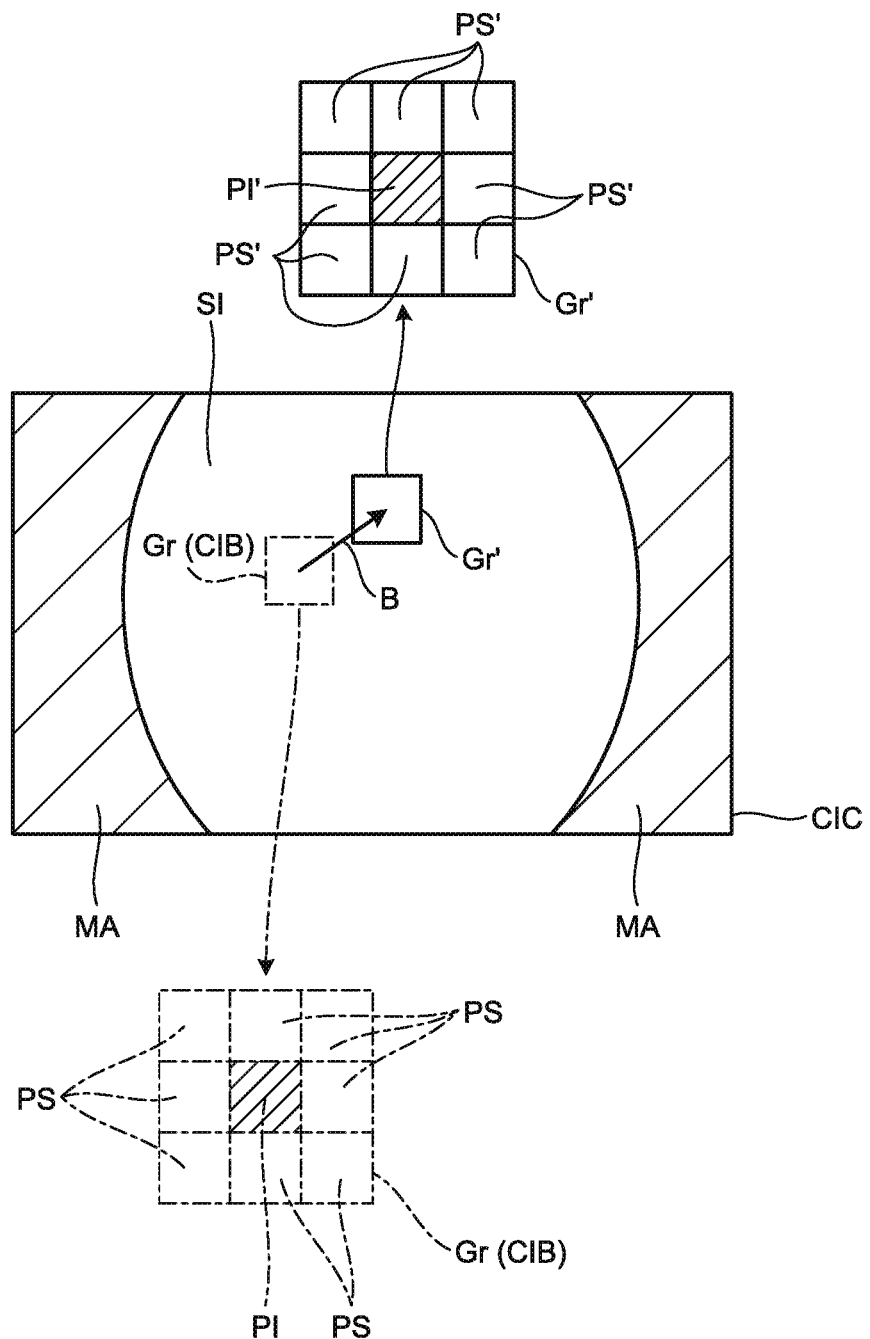
FIG. 5 is a diagram illustrating an example of a motion amount calculation process.
Figure 6:
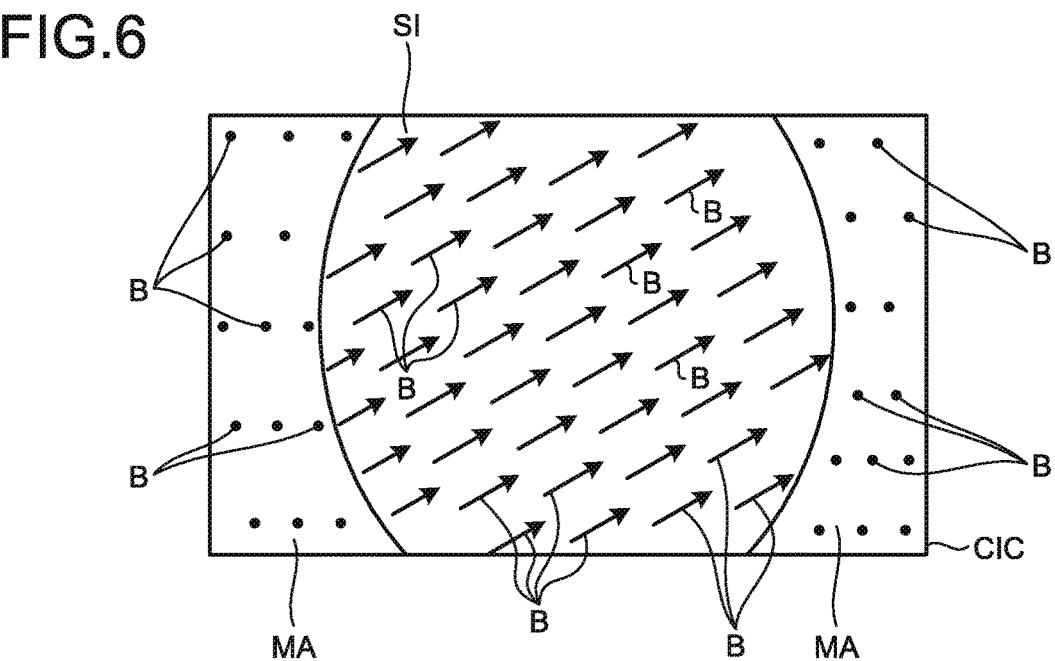
FIG. 6 is a diagram illustrating an example of a motion amount calculation process.

FIGS. 4 to 6 are diagrams for describing an example of the motion amount calculation process. Specifically, FIG. 4 is a diagram in which captured images CI1 to CI4 captured by the camera head 5 are arranged chronologically (in a direction of arrow t). Here, the light (subject image) which is reflected in the living organism and collected in the inserting unit 2 has a substantially circular cross section. Therefore, each of the captured images CI1 to CI4 includes a subject image SI and a mask area MA (indicated by hatching lines FIGS. 4 and 5) other than the subject image SI. FIGS. 5 and 6 are diagrams corresponding to FIG. 4 and illustrate current captured image CICs.

For example, as illustrated in FIGS. 5 and 6, the motion amount calculating unit 922 executes the motion amount calculation process using a block matching technique.

Specifically, the motion amount calculating unit 922 selects a pixel of interest PI (FIG. 5) among all pixels in a previous captured image CIB (FIG. 5). Also, the motion amount calculating unit 922 selects a pixel group Gr (FIG. 5) including the pixel of interest PI and a plurality of neighbor pixel PSs (FIG. 5) positioned around the pixel of interest PI. In the example of FIG. 5, the number of neighbor pixels PS is eight (the number of pixels in the pixel groups Gr is 9 (=3×3), but the number of neighbor pixels PS is not limited to eight, and it may be other numbers (for example, the number of neighbor pixels PS may be 24 (the number of pixels in the pixel group Gr is 25 (=5×5)).

Next, the motion amount calculating unit 922 specifies a pixel group Gr' (FIG. 5) which is highest in correlation with the pixel group Gr over the entire area of the current captured image CIC. The motion amount calculating unit 922 calculates a vector from the pixel of interest PI positioned at the center of the pixel group Gr in the previous captured image CIB to a pixel of interest PI' positioned at the center of the pixel group Gr' in the current captured image CIC as a motion vector B (FIG. 5) of the pixel of interest PI'.

The motion amount calculating unit 922 sequentially executes the processes described above while changing the pixel of interest PI for all pixels in the previous captured image CIB and calculates the motion vector B for each of (each pixel of interest PI') in the current captured image CIC as illustrated FIG. 6. In FIG. 6, a direction (direction of motion) of the motion vector B is indicated by an arrow, and a length (motion amount) of the motion vector B is indicated by a length of an arrow. The motion vector B indicated by a dot indicates that the motion amount is 0.

Note that the motion amount calculation process is not limited to the block matching technique described above, and other techniques (for example, a gradient technique) may be used.

The area specifying unit 923 executes an area specifying process of specifying the mask area MA in the current captured image CIC, a white flaw defect area WA (see FIG. 9) including a pixel of a white flaw defect, and a black flaw defect area BA (see FIG. 9) including a pixel of a black flaw defect. Here, when executing the area specifying process, specifically, the area specifying unit 923 refers to the motion amount of the pixel of interest PI' calculated by the motion amount calculating unit 922 and the motion amounts of the neighbor pixels PS' (FIG. 5) positioned around the pixel of interest PI' and the pixel level of the pixel of interest PI' and the pixel levels of the neighbor pixels PS' positioned around that pixel of interest PI' as will be specifically described later. The number of neighbor pixels PS' is not limited to eight and may be other numbers (for example, 24 or the like). Further, if the current captured image CIC is an image before the demosaic process by the signal correcting unit 925, component information (pixel value) of any one of R, G, and B corresponding to the filter groups of R, G, and B constituting the color filter 541a may be used as the pixel level. Further, if the current captured image CIC is an image which has undergone the demosaic process by the signal correcting unit 925, a luminance value corresponding to an RGB value (pixel value) or a Y signal (luminance signal) may be used as the pixel level. In other words, the area specifying process may be executed before the demosaic process by the signal correcting unit 925 or may be executed after the demosaic process by the signal correcting unit 925. Further, the area specifying process is not limited to the process of specifying the mask area MA, the white flaw defect area WA, and the black flaw defect area BA from all areas in the current captured image CIC, and a process of specifying the areas MA, WA, and BA from some areas among all areas in the current captured image CIC may be used.

The defect correction processing unit 924 executes a defect correction process of correcting a white flaw defect of each pixel in the white flaw defect area WA specified by the area specifying unit 923 and a black flaw defect of each pixel in the black flaw defect area BA specified by the area specifying unit 923 in the current captured image CIC.

Figure 7:
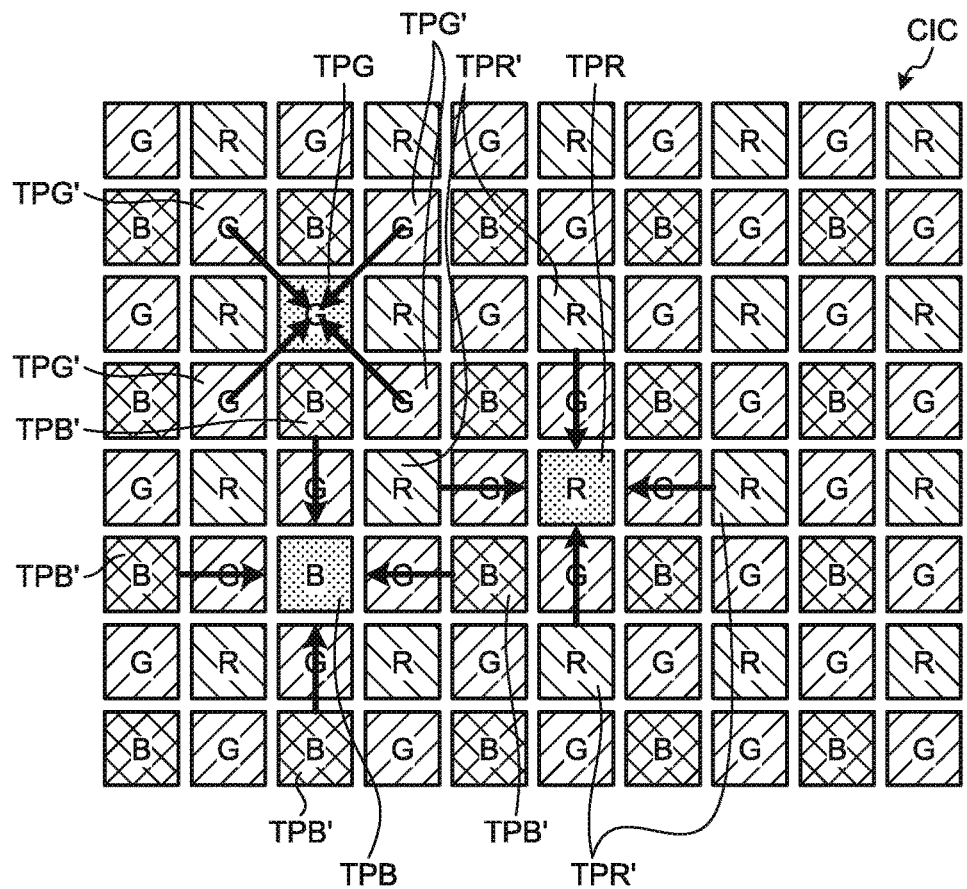
FIG. 7 is a diagram illustrating an example of a defect correction process.

FIG. 7 is a diagram for describing an example of the defect correction process. In FIG. 7, the current captured image CIC before the demosaic process by the signal correcting unit 925 is illustrated, and for convenience of description, a letter "R" is assigned to the pixel corresponding to the R filter group in the color filter 541a, a letter "G" is assigned to the pixel corresponding to the G filter group, and a letter "B" is assigned to the pixel corresponding to the B filter group. Further, in FIG. 7, dots are assigned to pixels (hereinafter referred to as target pixels TPR, TPG, and TPB) in the white flaw defect area WA and the black flaw defect area BA.

For example, a case in which the target pixel TPR is a pixel corresponding to R filter group in the color filter 541a is assumed. In this case, the defect correction processing unit 924 executes a defect correction process in which an average value of component information (pixel values) of R in four peripheral pixel TPR' adjacent to the target pixel TPR among pixels corresponding to R filter group is used as the pixel value of the target pixel TPR as indicated by an arrow in FIG. 7.

Also, for example, a case in which the target pixel TPG is the pixel corresponding to the G filter group in the color filter 541a is assumed. In this case, the defect correction processing unit 924 executes a defect correction process in which an average value of component information (pixel values) of G in four peripheral pixel TPG' adjacent to the target pixel TPG among pixels corresponding to G filter group is used as the pixel value of the target pixel TPG as indicated by an arrow in FIG. 7.

Further, for example, a case in which the target pixel TPB is a pixel corresponding to B filter group in the color filter 541a is assumed. In this case, the defect correction processing unit 924 executes a defect correction process in which an average value of component information (pixel values) of B in four peripheral pixel TPB' adjacent to the target pixel TPB among pixels corresponding to B filter group is used as the pixel value of the target pixel TPB as indicated by an arrow in FIG. 7.

In the above description, the number of peripheral pixels TPR', TPG', and TPB' used in the defect correction process is not limited to four, and other numbers of peripheral pixels TPR', TPG', and TPB' may be used. Further, although the case in which the defect correction process is executed before the demosaic process by the signal correcting unit 925 is exemplified above, the defect correction process may be executed after the demosaic process by the signal correcting unit 925.

The signal correcting unit 925 multiplies the image signal (the RAW signal (the digital signal)) by a digital gain for amplifying the digital signal. Further, the signal correcting unit 925 performs RAW processing such as an optical black subtraction process and the demosaic process on the image signal (the RAW signal (the digital signal)) multiplied by the digital gain, and converts the RAW signal (image signal) into an RGB signal (image signal). Further, the signal correcting unit 925 converts the RGB signal (image signal) into a luminance signal and a color difference signal (Y and $C_B/C_R$ signals). The signal correcting unit 925 performs correction processes such as a white balance adjustment process, gamma correction, contour enhancement, color tone correction, shading correction, and electronic mask process on the image signal (digital signal).

The NR processing unit 926 applies a time filter to the mask area MA specified by the area specifying unit 923 in the current captured image CIC, applies a space filter to the areas (the areas of the subject image SI) other than the mask area MA, and executes a noise reduction (NR) process of removing random noise in the current captured image CIC.

Based on a Y signal (luminance signal) of each pixel of a predetermined area (hereinafter referred to as a "detection area") in the entire current captured image CIC, the detection processing unit 927 executes detection of a contrast and a frequency component of an image in the detection area, detection of a luminance average value or a maximum/minimum pixel in the detection area by a filter or the like, comparison determination with a threshold value, detection of a histogram, or the like. Then, the detection processing unit 927 outputs detection information (the contrast, the frequency component, the luminance average value, the maximum/minimum pixel, the histogram, or the like) obtained by the detection to the control unit 94.

The display controller 93 generates a video signal for display based on the image signal (the Y and $C_B/C_R$ signals) processed by the image processing unit 92 under the control of the control unit 94. Then, the display controller 93 outputs the video signal to the display device 7 via the second transmission cable 8. Accordingly, the display device 7 displays the current captured image CIC based on the video signal.

The control unit 94 is configured by using, for example, a CPU, and outputs control signals via the first to third transmission cables 6, 8, and 10 to control the operations of the light source device 3, the camera head 5, and the display device 7 and control the operation of the entire control device 9. The control unit 94 includes a lens controller 941, a parameter calculating unit 942, and a brightness controller 943 as illustrated in FIG. 2.

The lens controller 941 operates the lens drive unit 52 to adjust the focus of the lens unit 51 (change the focus position).

For example, the lens controller 941 calculates a focus evaluation value for evaluating a focus state of the subject image SI included in the current captured image CIC based on the detection information (the contrast or the frequency component) output from the detection processing unit 927. Here, the lens controller 941 calculates the contrast detected by the detection processing unit 927 or a sum of high-frequency components among the frequency components detected by the detection processing unit 927 as the focus evaluation value. The focus evaluation value indicates that it is more focused as its value increases. Then, the lens controller 941 executes an AF process of positioning the focus lens 511 to the focus position at which the subject image SI is in the focus state by a hill climbing technique or the like based on the focus position detected by the lens position detecting unit 53 and the focus evaluation value.

Further, so-called continuous AF which is continuously executed or so-called one-touch AF which is executed in accordance with an operation of an operation button (not illustrated) installed in the camera head 5 or the like may be employed as the AD process.

The parameter calculating unit 942 calculates a brightness parameter for changing brightness of the current captured image CIC obtained by imaging by the imaging unit 54 to reference brightness (for changing the luminance average value obtained by the detection process to a reference luminance average value) based on the detection information (the luminance average value) output from the detection processing unit 927.

In the present embodiment, the parameter calculating unit 942 calculates four brightness parameters, that is, based on the detection information (the luminance average value) output from the detection processing unit 927, an exposure time of each pixel in the image sensor 541, an analog gain multiplied by the signal processing unit 542, a digital gain multiplied by the signal correcting unit 925, and a light quantity of light supplied from the light source device 3 to the inserting unit 2.

The brightness controller 943 controls the operations of the image sensor 541, the signal processing unit 542, the signal correcting unit 925, and the light source device 3 based on the brightness parameters calculated by the parameter calculating unit 942.

Specifically, the brightness controller 943 outputs the control signal to the imaging unit 54 via the first transmission cable 6, and uses the exposure time (brightness parameter) calculated by the parameter calculating unit 942 as the exposure time of each pixel of the image sensor 541. Further, the brightness controller 943 outputs the control signal to the imaging unit 54 via the first transmission cable 6, and uses the analog gain (brightness parameter) calculated by the parameter calculating unit 942 as the analog gain multiplied by the signal processing unit 542. Further, the brightness controller 943 outputs the control signal to the signal correcting unit 925, and uses the digital gain (brightness parameter) calculated by the parameter calculating unit 942 as the digital gain multiplied by the signal correcting unit 925. Further, the brightness controller 943 outputs the control signal to the light source device 3 via the third transmission cable 10, and uses the light quantity (brightness parameter) calculated by the parameter calculating unit 942 as the light quantity of the light supplied from the light source device 3 to the inserting unit 2.

As described above, the brightness controller 943 controls the operations of the image sensor 541, the signal processing unit 542, the signal correcting unit 925, and the light source device 3 such that the brightness of the current captured image CIC is changed to the reference brightness.

The input unit 95 is configured using an operation device such as a mouse, a keyboard, or a touch panel and receives a user operation by a user such as a doctor. Then, the input unit 95 outputs an operation signal corresponding to the user operation to the control unit 94.

The output unit 96 is configured using a speaker, a printer, or the like and outputs various information.

The storage unit 97 stores a program executed by the control unit 94, information necessary for processing of the control unit 94, and the like.

Operation of Control Device

Next, the operation of the control device 9 described above will be described.

Figure 8:
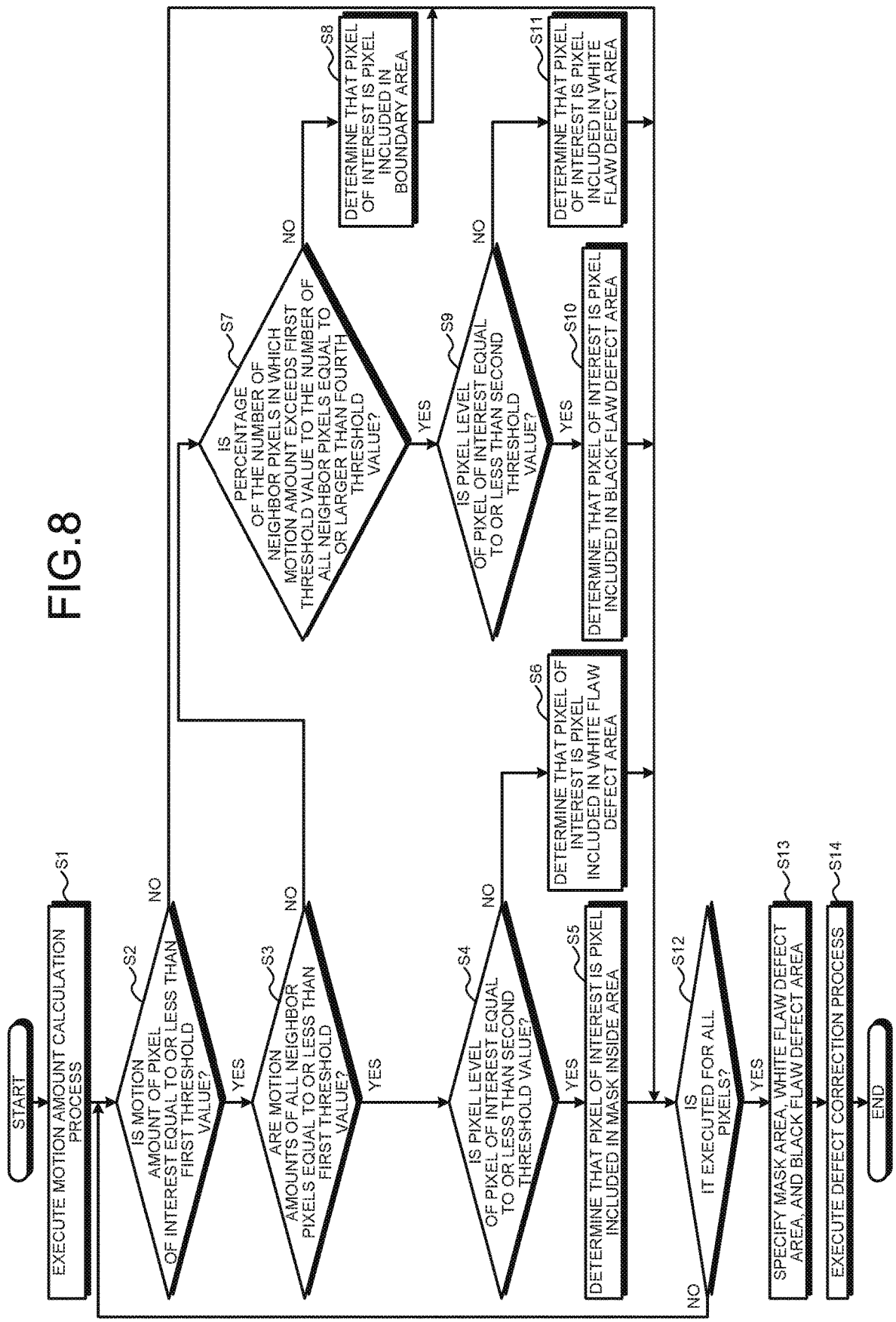
FIG. 8 is a flowchart illustrating an operation of a control device.
Figure 9:
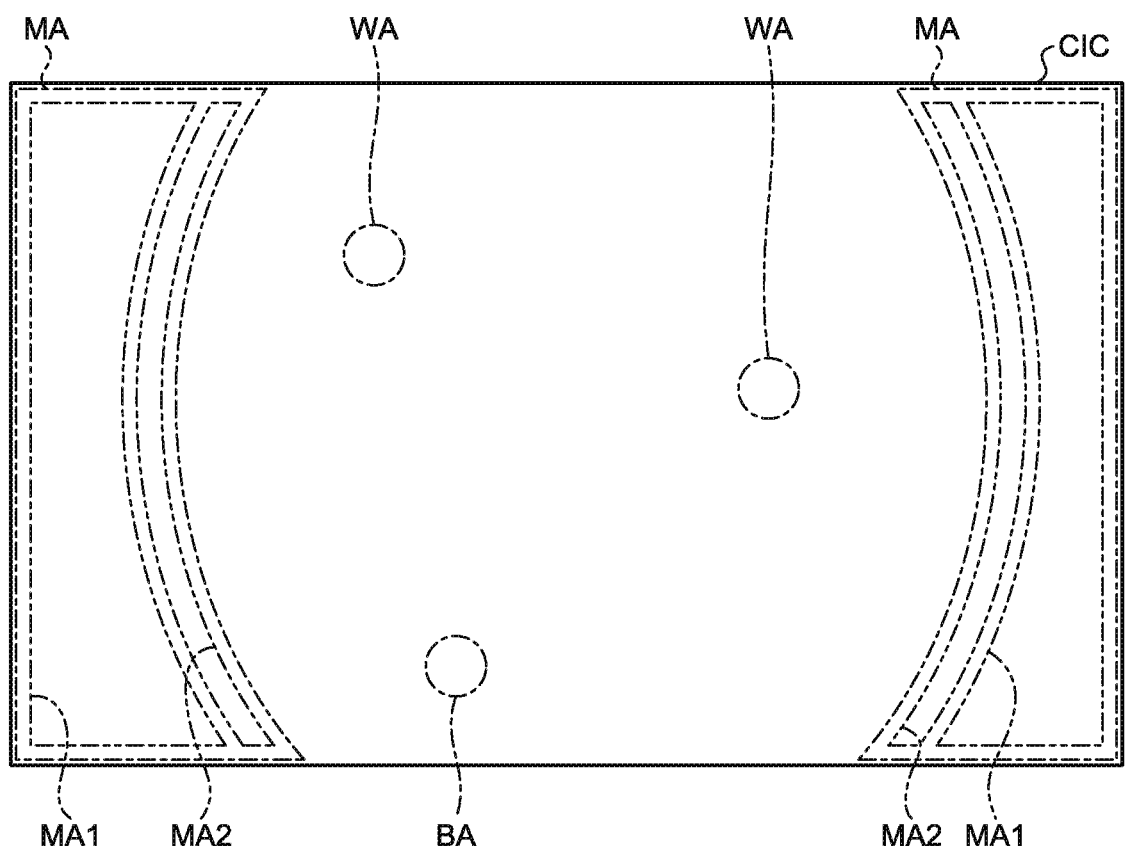
FIG. 9 is a diagram for explaining an operation of a control device.

FIG. 8 is a flowchart illustrating the operation of the control device 9. FIG. 9 is a diagram for describing the operation of the control device 9. Specifically, FIG. 9 is a diagram corresponding to FIG. 4 and illustrates the current captured image CIC.

Hereinafter, for convenience of description, the motion amount calculation process, the area specifying process, and the defect correction process will be described. Further, since the specific examples of the motion amount calculation process and the defect correction process have already been described, the area specifying process is mainly described below.

First, the motion amount calculating unit 922 executes the motion amount calculation process (Step S1).

After Step S1, the area specifying unit 923 determines whether or not the motion amount of the pixel of interest PI' calculated in Step S1 is equal to or less than a first threshold value for one pixel of interest PI' serving as an area specifying target among pixels in the current captured image CIC (Step S2).

When it is determined that the motion amount of pixel of interest PI' exceeds the first threshold value (Step S2: No), the control device 9 proceeds to Step S12.

On the other hand, when it is determined that the motion amount of the pixel of interest PI' is equal to or less than the first threshold value (Step S2: Yes), the area specifying unit 923 determines whether or not the motion amounts of all the neighbor pixels PS' calculated in Step S1 are equal to or less than the first threshold value for all the neighbor pixels PS' (eight neighbor pixels PS' in the example of FIG. 5) positioned around the pixel of interest PI' (Step 3). The first threshold value corresponds to a first threshold value according to the present disclosure and corresponds to a third threshold value.

When it is determined that the motion amounts of at least some neighbor pixels PS' exceed the first threshold value (Step S3: No), the control device 9 proceeds to Step S7.

On the other hand, when it is determined that the motion amount of all neighbor pixel PS's is equal to or less than the first threshold value (Step S3: Yes), the area specifying unit 923 determines whether or not the pixel level of the pixel of interest PI' is equal to or less than a specific second threshold value (Step S4). The second threshold value corresponds to a fifth threshold value in addition to a second threshold value according to the present disclosure.

When it is determined that the pixel level of the pixel of interest PI' is equal to or less than the second threshold value (Step S4: Yes), the area specifying unit 923 determines that the pixel of interest PI' is a pixel included in a mask inside area MA1 (FIG. 9) (Step S5). The mask inside area MA1 is the mask area MA and is an area in which a boundary area MA2 positioned at the boundary between the mask area MA and the subject image SI is excluded. Thereafter, the control device 9 proceeds to Step S12.

On the other hand, when it is determined that the pixel level of pixel of interest PI' exceeds the second threshold value (Step S4: No), the area specifying unit 923 determines that the pixel of interest PI' is a pixel included in the white flaw defect area WA (Step S6). Thereafter, the control device 9 proceeds to Step S12.

In Step S7, the area specifying unit 923 determines whether or not a percentage described below is equal to or larger than a specific fourth threshold value. The percentage is a percentage of the number of neighbor pixels PS' in which the motion amount calculated in Step S1 exceeds the first threshold value among all the neighbor pixels PS' to the number of all neighbor pixels PS' (eight in the example of FIG. 5).

When it is determined that the percentage is less than the fourth threshold value (Step S7: No), the area specifying unit 923 determines that the pixel of interest PI' is a pixel included in the boundary area MA2 (Step S8). Thereafter, the control device 9 proceeds to Step S12.

On the other hand, when it is determined that the percentage is equal to or larger than the fourth threshold value (Step S7: Yes), the area specifying unit 923 determines whether or not the pixel level of the pixel of interest PI' is equal to or less than the second threshold value, similarly to Step S4 (Step S9). The second threshold value corresponds to a sixth threshold value in addition to the second and fifth threshold values according to the present disclosure.

When it is determined that the pixel level of the pixel of interest PI' is equal to or less than the second threshold value (Step S9: Yes), the area specifying unit 923 determines that the pixel of interest PI' is a pixel included in the black flaw defect area BA (Step S10). Thereafter, the control device 9 proceeds to Step S12.

On the other hand, when it is determined that the pixel level of the pixel of interest PI' exceeds the second threshold value (Step S9: No), the area specifying unit 923 determines that the pixel of interest PI' is a pixel included in the white flaw defect area WA, similarly to Step S6 (Step S11). Thereafter, the control device 9 proceeds to Step S12.

In Step S12, the area specifying unit 923 determines whether or not Steps S2 to S11 have been executed by regarding all the pixels in the current captured image CIC as the pixel of interest PI'.

When it is determined that the process is not performed on any one of all the pixels (Step S12: No), the area specifying unit 923 changes the pixel of interest PI' and returns to Step S2.

On the other hand, when it is determined that the process has been performed on all the pixels (Step S12: Yes), the area specifying unit 923 specifies the mask area MA, the white flaw defect area WA, and the black flaw defect area BA of the current captured image CIC based on the determination results of Steps S5, S6, S8, S10, and S11 as illustrated in FIG. 9 (Step S13). As described above, the mask area MA is constituted by the mask inside area MA1 and the boundary area MA2. Also, the area constituted by the mask area MA, the white flaw defect area WA, and the black flaw defect area BA corresponds to a mask candidate area according to the present disclosure.

After Step S13, the defect correction processing unit 924 executes the defect correction process for each pixel in the white flaw defect area WA and the black flaw defect area BA specified in Step S13 in the current captured image CIC (Step S14).

Note that the detection processing unit 927 executes the detection process after Step S14. Specifically, the detection processing unit 927 acquires the luminance signal (Y signal) among the image signals (the Y and $C_B/C_R$ signals) processed by the signal correcting unit 925. Further, the detection processing unit 927 sets the area of the subject image SI excluding the mask area MA specified in Step S13 as the detection area. Then, the detection processing unit 927 executes the detection process based on the luminance signal (Y signal) of each pixel of the detected area among the acquired luminance signals (Y signals). Further, the control unit 94 executes the AF process, calculation of the brightness parameter, operation control or the like of the image sensor 541, the signal processing unit 542, the signal correcting unit 925, and the light source device 3 based on the brightness parameter based on the detection information obtained by the detection process.

Further, after Step S14, the signal correcting unit 925 executes the electronic mask process of covering the mask area MA specified in Step S13 in the current captured image CIC with black. Here, in the above example, in Step S14, in addition to the white flaw defect included in the area of the subject image SI, the white flaw defect included in the mask area MA is corrected, but the present disclosure is not limited to this example, and only the white flaw defect included in the area of the subject image SI may be corrected. With the above-described configuration, the processing load of the defect correction processing unit 924 may be reduced because the area in which the defect correction process is executed is reduced.

The signal correcting unit 925 may increase an emphasis degree in an emphasizing process such as outline emphasis as the size of the mask area MA specified in Step S13 decreases (as the size of the subject image SI increases). Also, the signal correcting unit 925 may be configured to execute shading correction when the size of the mask area MA specified in Step S13 is equal to or less than a predetermined threshold value (when the size of the subject image SI equal to or larger than a predetermined threshold value).

According to the present embodiment described above, the following effects may be obtained.

The present disclosure is focused on a point that, since the mask area MA is an area generated due to the inserting unit 2, even when the inserting unit 2 moves, there is a motion in the subject image SI in the current captured image CIC, but there is not motion in the mask area MA at all. Further, the control device 9 according to the present embodiment specifies the mask area MA included in the current captured image CIC from an inside of a mask candidate area in which the motion amount is less than the first threshold value among all the areas in the current captured image CIC. In other words, since it is possible to specify the mask area MA based on the motion amount, it is not necessary to cover the distal end of the inserting unit 2 with a white subject such as a gauze. Further, it possible to specify the mask area MA with high accuracy because it is sufficient if an area having no motion is specified as the mask area MA. Therefore, according to the control device 9 of the present embodiment, the mask area MA may be specified easily with high accuracy.

Also, the present disclosure is also focused on a point that, since the white flaw defect area WA is an area including the pixel of the white flaw defect in the image sensor 541, even when the inserting unit 2 moves, there is no motion in the white flaw defect area WA in the current captured image CIC at all. Further, the control device 9 according to the present embodiment specifies the area which is the mask candidate area and includes the pixel whose pixel level exceeds the second threshold value among all the areas in the current captured image CIC as the white flaw defect area WA and executes the defect correction process on the white flaw defect area WA. In other words, it is possible to specify the white flaw defect area WA which is an area having no motion and has a relatively high pixel level with high accuracy and execute the defect correction process on the white flaw defect area WA satisfactorily.

By the way, in the pixel of interest PI' included in the mask inside area MA1 in the mask area MA, the motion amounts of all the neighbor pixels PS' are equal to or less than the first threshold value. On the other hand, in the mask area MA, the pixel of interest PI' included in the boundary area MA2 has the area of the subject image SI therearound, and thus the motion amounts of some neighbor pixels PS' exceed the first threshold value. Also, the pixel of interest PI' included in the boundary area MA2 has a relatively small percentage of the number of neighbor pixels PS' in which the motion amount exceeds the first threshold value with respect to the numbers of all neighbor pixels PS'. On the other hand, the pixel of interest PI' included in the area of the subject image SI has a relatively large percentage.

The control device 9 according to the present embodiment executes Steps S2, S3, and S7 focusing on the above relations. Therefore, it is possible to clearly separate the boundary area MA2 and the area of the subject image SI.

Also, the present disclosure is also focused on a point that, since the black flaw defect area BA is an area including the pixel of the black flaw defect in the image sensor 541, even when the inserting unit 2 moves, there is no motion in the black flaw defect area BA in the current captured image CIC at all. Then, the control device 9 according to the present embodiment executes Steps S2, S3, S7, S9, and S13, specifies the black flaw defect area BA, and executes the defect correction process on the black flaw defect area BA in Step S14. In other words, it is possible to specify the black flaw defect area BA which is an area having no motion and has a relatively low pixel level with high accuracy and execute the defect correction process on the black flaw defect area BA satisfactorily.

In particular, the control device 9 according to the present embodiment corrects only the black flaw defect included in the area of the subject image SI in Step S14. Therefore, since the area in which the defect correction process is executed decreases as compared with the configuration that corrects the black flaw defect included in the mask area MA, the processing load of the defect correction processing unit 924 may be reduced.

Moreover, the control device 9 according to the present embodiment executes the detection process using the area of the subject image SI other than the mask area MA identified by the area specifying unit 923 among all the areas in the current captured image CIC as the detection area.

Therefore, it is possible to execute the detection process in the widest detection area (substantially the entire area of the subject image SI)) not including the mask area MA. In other words, it is possible to execute the process based on the detection information obtained by the detection process (for example, the AF process or the brightness parameter calculation process, or the like) with high accuracy.

Other Embodiments

Although the mode for carrying out the present disclosure has been described above, the present disclosure should not be limited only by the embodiment described above.

Figure 10:
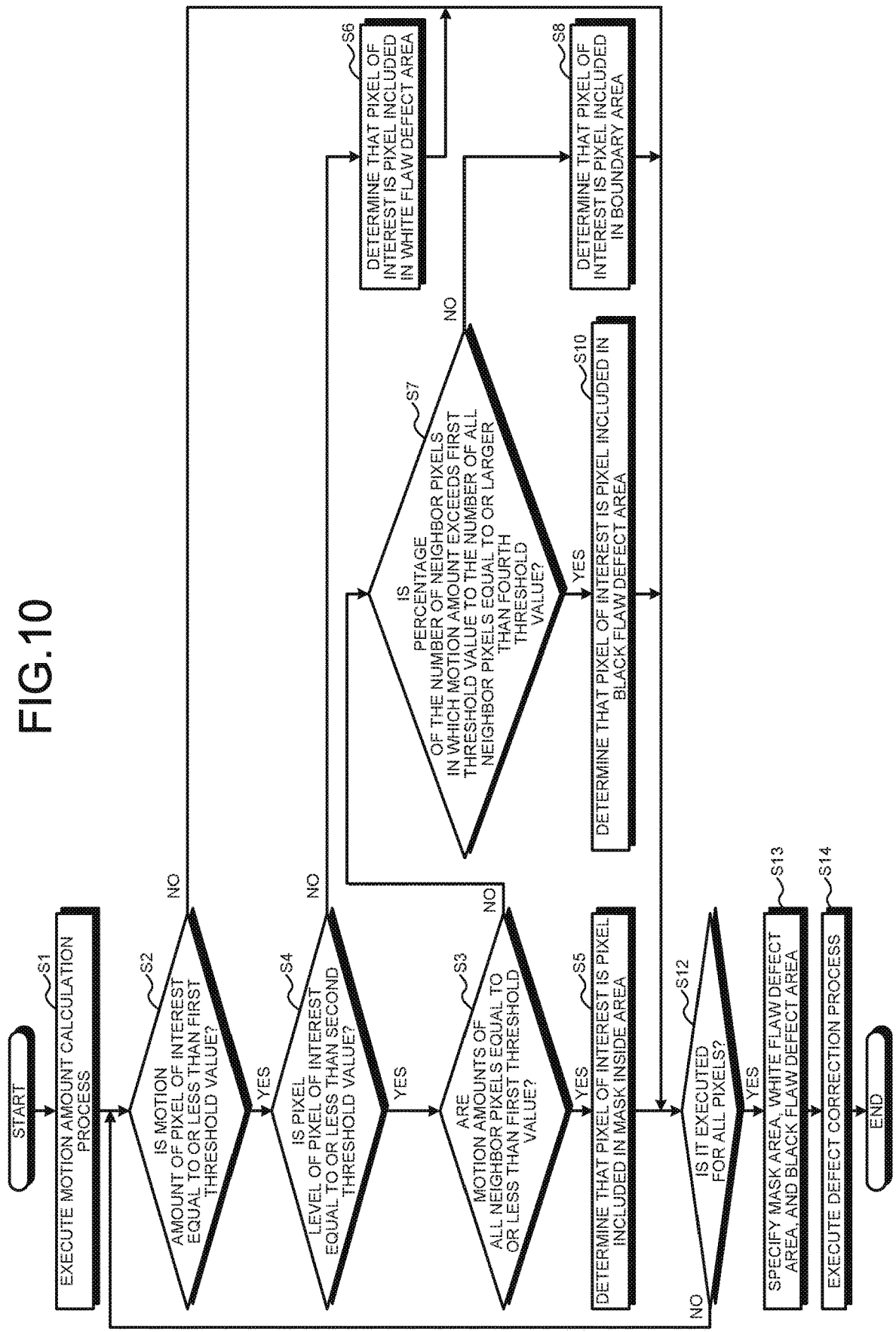
FIG. 10 is a diagram illustrating a modified example of an embodiment.

FIG. 10 is a diagram illustrating a modified example of the present embodiment.

In the embodiment described above, the area specifying process is not limited to the flow illustrated in FIG. 8, and the processing order may be changed as long as there is no contradiction.

For example, the flow illustrated in FIG. 10 may be employed. Specifically, in the flow illustrated in FIG. 10, Steps S9 and S11 are omitted from the flow illustrated in FIG. 8, and the order of Step S3 and Step S4 is reversed.

In the embodiment described above, the first and third threshold values according to the present disclosure have the same value, and the second, fifth, and sixth threshold values according to the present disclosure have the same value, but the present disclosure is not limited thereto, and the first to sixth threshold values according to the present disclosure may all be different values.

In the above embodiment, the motion amount according to the present disclosure is calculated by the block matching technique or the gradient technique, but the present disclosure is not limited thereto.

For example, the pixel levels of the pixels of the first and second images of the present disclosure are compared. Then, an amount of change in the pixel level may be calculated as the motion amount according to the present disclosure. In this case, in addition to the configuration in which the motion amount is calculated for each pixel, the motion amount may be calculated for each pixel group (area) including a plurality of pixels. The same applies to the embodiment described above.

In the embodiment described above, the color filter 541a is installed in the image sensor 541, but the present disclosure is not limited thereto. For example, a so-called monochrome sensor with no color filter 541a may be used as the image sensor 541. Also, it may be constituted by three boards of an image sensor for R, an image sensor for G, and an image sensor for B.

In the embodiment described above, some components of the camera head 5 and some components of the control device 9 may be installed in, for example, the connector CN1 or the connector CN2.

According to a medical image processing device and a medical observation device according to the present disclosure, it is possible to specify the mask area easily and accurately.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
processing circuitry configured to:
compare a first image obtained by capturing a subject image taken by an endoscope with a second image obtained by capturing the subject image at a chronologically different timing from the first image and calculate a motion amount for the second image in at least two areas in the first image; and
specify an area which a mask area other than the subject image included in the first image from an inside of a mask candidate area in which the motion amount is equal to or less than a specific first threshold value in the first image, wherein the area is the mask candidate area and includes a pixel whose pixel level exceeds a specified second threshold value in the first image as a white flaw defect area.

2. The medical image processing device according to claim 1, wherein the processing circuitry is further configured to perform white flaw defect correction of correcting a white flaw defect on the white flaw defect area.

3. The medical image processing device according to claim 2, wherein the processing circuitry is further configured to:
execute an electronic mask process of covering the mask area with black, and execute the white flaw defect correction on the white flaw defect area included in an area other than the mask area specified in the first image.

4. The medical image processing device according to claim 1, wherein the processing circuitry is configured to specify, as a boundary area positioned between the subject image and the mask area, an area which is the mask candidate area in the first image in a case in which a pixel which is an area specifying target in the first image is set as a pixel of interest, and pixels positioned around the pixel of interest are set as neighbor pixels and includes the pixel of interest in which the motion amounts of some of the neighbor pixels exceed a specific third threshold value and the pixel of interest in which a percentage of the number of neighbor pixels in which the motion amount exceeds the third threshold value with respect to the number of all the neighbor pixels is less than a specific fourth threshold value.

5. The medical image processing device according to claim 4, wherein the processing circuitry is configured to specify, as the mask area, an area which is the mask candidate area in the first image and includes the pixel of interest in which the motion amounts of all the neighbor pixels are equal to or less than the third threshold value and the pixel of interest in which a pixel level is equal to or less than a specific fifth threshold value and the boundary area.

6. The medical image processing device according to claim 4, wherein the processing circuitry is configured to specify, as a black flaw defect area, an area which is the mask candidate area in the first image and includes the pixel of interest in which a percentage of the number of neighbor pixels in which the motion amount exceeds the third threshold value with respect to the number of all the neighbor pixels is equal to or larger than the fourth threshold value and the pixel of interest in which a pixel level is equal to or less than a specific sixth threshold value.

7. The medical image processing device according to claim 6, wherein the processing circuitry is configured to execute a black flaw defect correction of correcting a black flaw defect on the black flaw defect area.

8. The medical image processing device according to claim 7, wherein the processing circuitry is configured to execute the black flaw defect correction on the black flaw defect area included in an area other than the mask area specified in the first image.

9. The medical image processing device according to claim 1, wherein the processing circuitry is configured to:
execute a detection process for calculating a brightness parameter used for changing brightness in the first image, and
execute the detection process based on a luminance signal of each pixel in an area other than the mask area specified in the first image.

10. The medical image processing device according to claim 1, wherein the processing circuitry is configured to:
execute a detection process for controlling an imaging device that captures the subject image and generate the first image and the second image, and
execute the detection process based on a luminance signal of each pixel in an area other than the mask area specified in the first image.

11. A medical observation device comprising:
an endoscope inserted into a subject;
imaging circuitry that is detachably connected to an eyepiece of the endoscope and captures a subject image taken by the endoscope; and
the medical image processing device according to claim 1, the medical image processing device that processes an image captured by the imaging circuitry.

12. A medical image processing device comprising:
processing circuitry configured to:
compare a first image obtained by capturing a subject image taken by an endoscope with a second image obtained by capturing the subject image at a chronologically different timing from the first image and calculate a motion amount for the second image in at least two areas in the first image; and
specify an area which a mask area other than the subject image included in the first image from an inside of a mask candidate area in which the motion amount is equal to or less than a specific first threshold value in the first image, wherein, as a boundary area positioned between the subject image and the mask area, an area which is the mask candidate area in the first image in a case in which a pixel which is an area specifying target in the first image is set as a pixel of interest, and pixels positioned around the pixel of interest are set as neighbor pixels and includes the pixel of interest in which the motion amounts of some of the neighbor pixels exceed a specific third threshold value and the pixel of interest in which a percentage of the number of neighbor pixels in which the motion amount exceeds the third threshold value with respect to the number of all the neighbor pixels is less than a specific fourth threshold value.

\* \* \* \* \*